United States Patent [19]

Ambrose et al.

[11] Patent Number: 4,636,201
[45] Date of Patent: Jan. 13, 1987

[54] HYPODERMIC SYRINGE HAVING A PROTECTIVE SHEATH COVER

[75] Inventors: William A. Ambrose, Crystal Lake; Fernando A. Garcia, Vernon Hills, both of Ill.

[73] Assignee: American Hospital Supply Corporation, Evanston, Ill.

[21] Appl. No.: 793,878

[22] Filed: Nov. 1, 1985

[51] Int. Cl.$^4$ .............................................. A61M 5/32
[52] U.S. Cl. .................................... 604/192; 604/263
[58] Field of Search ................ 604/263, 192, 193, 187

[56] References Cited

U.S. PATENT DOCUMENTS

| | | |
|---|---|---|
| 2,737,949 | 3/1956 | Brown . |
| 3,050,059 | 8/1962 | Wall et al. . |
| 3,253,592 | 5/1966 | Von Pechmann . |
| 4,317,446 | 3/1982 | Ambrosio et al. ................... 604/193 |
| 4,430,082 | 2/1984 | Schwabacher ...................... 604/263 |

Primary Examiner—John D. Yasko
Attorney, Agent, or Firm—Gildo E. Fato

[57] ABSTRACT

Described is a hypodermic syringe which includes provision for a rigid sheath cover or sleeve which encompasses the rubber needle cover and provides protection in the operating mode as well as other advantages. The rubber needle cover is placed over the needle and provides a sterile barrier for the needle after the syringe unit is sterilized.

The sheath cover can be made of plastic and includes a plurality of teeth spaced about the opening of the cover. At least some of the teeth have a small lip projecting inwardly from the end of the teeth toward the center of the opening. When the rigid sleeve is inserted over the rubber needle cover, the lips slip over the cover to grip it so that when the sleeve is removed, the rubber cover is retained within the sleeve and the two are removed together. After the medicament is administered, the needle cover and sheath are replaced. In the event the needle pierces the rubber needle cover, the sheath prevents the needle from protruding, thereby providing protection for the user. The sheath cover also protects the rubber sleeve from light thereby preventing cracking.

8 Claims, 5 Drawing Figures

HYPODERMIC SYRINGE HAVING A PROTECTIVE SHEATH COVER

BACKGROUND OF THE INVENTION

Prefilled hypodermic syringes generally include a rubber needle cover which is placed over the needle in engagement with the needle hub or shoulder which projects from the syringe barrel. The cover is placed over the needle during manufacture of the syringe and provides a sterile barrier, maintaining sterility until the syringe is used. In use, the rubber needle cover is removed, air is expelled from the needle, and the medication is administered. The needle cover is then replaced. In other situations, after the air and excess drug is expelled from the syringe, the rubber needle cover is placed back onto the syringe for protection until ready to administer the drug. In replacing the rubber needle cover after drawing the medication into the syringe, the syringe needle tends to protrude through the side of the rubber needle cover, particularly under emergency conditions, sometimes puncturing the finger of the nurse or paramedic. This oftentimes requires submission of a report, testing of the nurse, discomfort and other problems. Some means of protecting the user of such syringes would therefore be desirable. Rubbler needle covers are also used with syringes which are provided empty and sterile. These are used to administer drug from a vial or ampul. In use, the rubber needle cover is removed and the medication is drawn into the syringe form the vial or ampul. The cover is then replaced until the syringe is used to administer the drug to the patient.

SUMMARY OF THE INVENTION

Described is a hypodermic syringe which includes provision for a rigid sheath cover or sleeve which encompasses the rubber needle cover and provides protection in the operating mode as well as other advantages. The sheath cover can be made of plastic by injection molding procedures and includes a plurality of teeth spaced about the opening of the cover. At least some of the teeth have a small lip projecting inwardly from the end of the teeth toward the center of the opening. When the rigid sleeve is inserted over the rubber needle cover, the lips slip over the cover to grip it so that when the sleeve is removed, the rubber cover is retained within the sleeve and the two are removed together. After the medicament is administered, the needle cover and sheath are replaced. In the event the needle pierces the rubber needle cover, the sheath prevents the needle from protruding, thereby providing protection for the user. The sheath cover has additional advantages. Rubber formulations, such as those used to make the rubber needle covers, are generally sensitive to light and will crack over time. With a hypodermic syringe, this may compromise the sterility of the needle in storage. By providing an opaque plastic sheath cover, the cover will protect the rubber sleeve from light thereby preventing cracking. The sheath cover can also be used for imprinting of the syringe lot number and expiration date as well as other information and can be made in different colors for color coding of products. The plastic sheath also facilitates the "breaking off" of the needle for injections via stop cocks.

The protective sheath cover has other advantages such as providing dimensional stability to the rubber needle cover. The rubber needle cover is held loosely but securely within the protective sheath cover so that the rubber needle cover is straight as it is being replaced over the straight needle. This minimizes the possibility of the needle piercing the rubber cover and prevents possible injury as previously described. Likewise, if the needle point catches on the inside of a non-supported rubber cover, it may bend the needle point. A dull or bent needle point creates patient discomfort and other administration problems.

When the needle protrudes from the rubber cover, the sterility of the needle is in question. Possible "coring" of the rubber is another problem. Since the administration of medication should not be made with a non-sterile needle nor with one containing a rubber core, it can be expected that the syringe will be unsuitable and another syringe will have to be obtained. In an emergency situation, much valuable time could be lost obtaining another syringe. The protective sheath cover provides cost savings by minimizing product made unusable by "coring" as indicated above.

BRIEF DESCRIPTION OF THE DRAWINGS

The invention will be better understood by reference to the following detailed description when considered in connection with the accompanying drawings wherein.

DETAILED DESCRIPTION OF THE INVENTION

Figure 1:
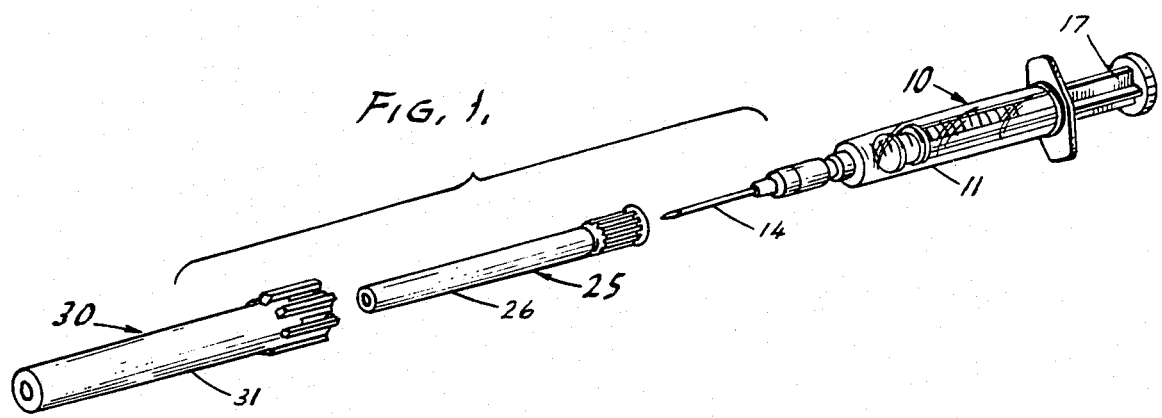
FIG. 1 is an exploded, isometric view illustrating a hypodermic syringe, needle cover and sheath cover.
Figure 2:
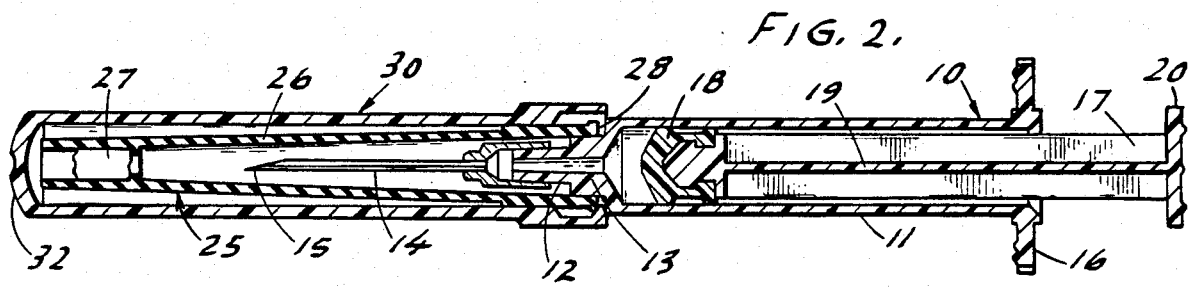
FIG. 2 is a longitudinal sectional view taken axially through the assembled syringe needle cover and sheath cover.

Referring to the drawings in detail, a preferred embodiment of the present invention is illustrated therein. As illustrated in FIGS. 1 and 2, a complete syringe assembly is depicted comprising a syringe 10, needle cover 25, and sheath cover 30.

Referring to FIG. 2, the conventional hypodermic syringe 10 comprises a barrel 11, including a needle hub 12 at one end thereof, the barrel as illustrated including a shoulder 13. Sealed into the needle hub 12 is a needle 14 having a point 15 at the distal end thereof. A flange or finger grip 16 projects from the end of the barrel 11 opposite the needle hub 12. A plunger 17 is slideably engaged with the inside of the barrel 11, and comprises a body 18 which is sealingly engaged with the inside of the barrel 11, a stem 19 projecting outwardly from the body 18 and including a tab or thumb rest 20 on the end thereof opposite the body 18.

The rubber needle cover 25 comprises a hollow tubular body 26 having a closed end 27 and an open end 28. The open end 28 of the needle cover 25 is adapted for sealingly engaging the shoulder 13 on the barrel 11. The rubber needle cover 25 provides a sterile barrier for the needle 14 after the syringe unit 10 is sterilized.

Figure 3:
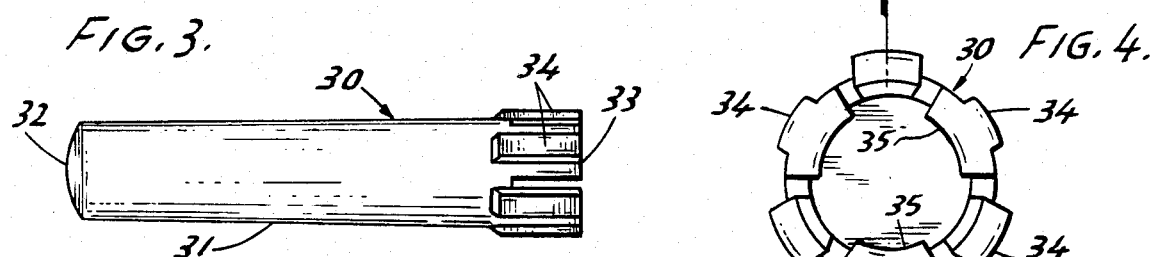
FIG. 3 is a side elevational view of the sheath cover.
Figure 4:
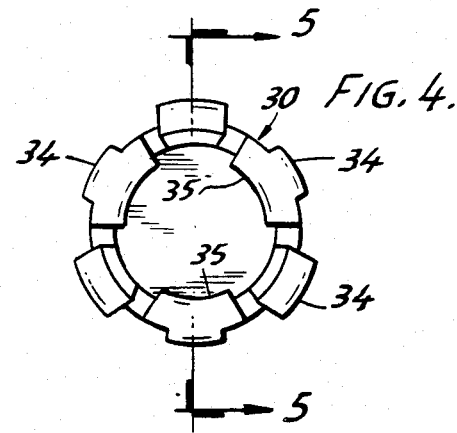
FIG. 4 is an end elevational view of the opening in the sheath cover particularly illustrating the plurality of teeth, some including a lip projecting toward the center of the opening.
Figure 5:
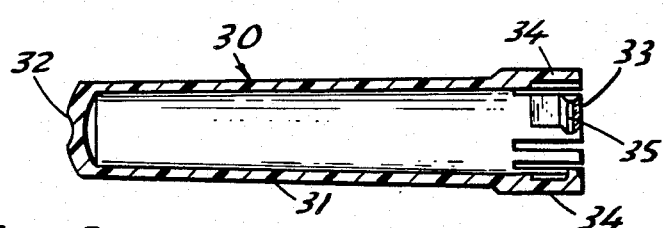
FIG. 5 is a side cross-sectional view as viewed along the line 5—5 of FIG. 4.

The rigid sheath cover or sleeve 30, as can be best seen in FIGS. 3, 4 and 5, comprises a hollow tubular body 31 having a closed end 32 and an open end 33 and is substantially coextensive in length with the length of the needle cover 25. The open end includes a plurality of spaced projecting teeth 34 projecting outwardly from the body 31 to form the open end 33. Some of the teeth 34 have a small lip 35 on the end thereof projecting inwardly toward the center of the opening 33 formed by the teeth 34. The lips 35 together with the projecting teeth 34 on which they are formed are adapted to grip the needle cover 25 to remove and replace the needle cover 25 as hereinafter described. Preferably, lips 35 are included on at least three of the projecting teeth 34, in an opposing relationship, so as to aid in effectively gripping the needle cover 25. In the embodiment illustrated, the sheath cover 30 includes a total of six spaced teeth 34, each alternate tooth 34 including a lip 35, as best seen in FIG. 4. Moreover, the teeth 34 are offset from the tubular body 31, in a longitudinal direction, as best seen in FIGS. 3 and 5.

After the hypodermic syringe 10 is fabricated by the manufacturer, the syringe 10 is sterilized and the rubber needle cover 25 is placed over the needle 14, the open end 28 engaging the shoulder 13 on the barrel 11 of the syringe 10 in a sealing fashion thereby providing a sterile barrier for the needle 14. After the syringe 10 is filled with a medicament, the sheath 30 is placed over the needle cover 25 as hereinafter described.

In use, when the sheath 30 is inserted over the rubber needle cover 25, the lips 35 slip over the open end 28 of the rubber needle cover 25 to grip the cover, as is best seen in FIG. 2, so that when the sheath 30 is removed, the rubber needle cover 25 is retained with the sheath 30 and is removed from the syringe barrel 11 together with the sheath 30. When the sheath 30 and needle cover 25 are replaced on the syringe 10, the sheath prevents the needle 14 from protruding in the event it punctures the rubber needle cover 25. The needle cover 25, fabricated from rubber, is light sensitive and consequently, is prone to cracking, thereby jeopardizing the sterility of the needle 14. The sheath 30 therefore provides a further advantage in that it minimizes the effect of light on the rubber needle cover 25. By making the sheath opaque, the effect of light is diminished even more.

In molding the sheath 30, the lip 35 causes problems of removal of the molded sheath from the mold, namely, in that the lip 35 has to ride over the core. In practice, the design as illustrated permits satisfactory removal of the sheath 30 from the mold. This is opposite to the usual experience in injection molding of such a part. It is preferable to use styrene plastic in molding the sheath 30 since it is imprintable and therefore can be printed with various desirable information. It has been found that nylon or modified nylon is unsuitable for molding the sheath 30 since the teeth 34 easily break off in removal of the molded sheath 30 from the mold.

What is claimed is:

1. A rigid sheath cover adapted to be placed over a hypodermic syringe needle cover, the sheath cover comprising:
   a hollow tubular body having a closed end and an opposing open end;
   a plurality of spaced teeth projecting outwardly from the tubular body to form the open end;
   the sheath cover being substantially coextensive in length with the length of the needle cover;
   a lip on the end of at least two of the teeth projecting inwardly toward the center of the opening in the open end formed by the projecting teeth;
   said spaced teeth and lips being adapted to grip the needle cover when the sheath is placed over the needle cover whereby the needle cover is removed together with the sheath when the sheath is removed from the hypodermic syringe and is retained within the sheath when the sheath and needle cover are replaced on the syringe.

2. The sheath cover of claim 1 wherein at least three of the spaced teeth, arranged in an opposing relationship, include a lip.

3. The sheath cover of claim 1 wherein said cover includes six spaced projecting teeth, each alternate tooth including a lip.

4. The sheath cover of claim 3 wherein the surface of said cover is adapted to receive imprinting.

5. The sheath cover of claim 4 wherein said cover is molded of a styrene plastic.

6. A hypodermic syringe comprising a barrel including a needle hub at one end thereof together with a projecting shoulder; a needle molded into the hub and projecting outwardly from the barrel; a plunger slideably engageable with the inside of the barrel; a needle cover positioned over the needle and sealingly engaging the shoulder on the barrel to provide a sterile barrier for the needle after the syringe is sterilized; and a rigid sheath cover positioned over the needle cover, the sheath cover comprising a hollow tubular body having a closed end and an opposing open end; a plurality of spaced teeth projecting outwardly from the tubular body to form the open end; a lip on the end of at least two of the teeth and projecting inwardly toward the center of the opening in the open end formed by the projecting teeth; said spaced teeth and lips being adapted to grip the needle cover when the sheath is placed over the needle cover whereby the needle cover is removed together with the sheath when the sheath is removed from the hypodermic syringe and is retained within the sheath when the sheath and needle cover are replaced on the syringe.

7. The hypodermic syringe of claim 6 wherein said sheath cover includes at least three spaced teeth having a lip thereon, said teeth arranged in an opposing relationship.

8. The hypodermic syringe of claim 7 wherein said sheath cover includes six spaced, projecting teeth, each alternate tooth including a lip.

* * * * *